(12) United States Patent
Yen et al.

(10) Patent No.: US 9,482,784 B2
(45) Date of Patent: Nov. 1, 2016

(54) IMAGING METAMATERIAL FOR PROJECTING AN OBJECT IMAGE WITH MOLECULAR AND REFRACTIVE INDEX SIGNAL

(71) Applicants: Ta-Jen Yen, Hsinchu (TW);
Cheng-Kuang Chen, Hsinchu (TW);
Yueh-Chun Lai, Hsinchu (TW)

(72) Inventors: Ta-Jen Yen, Hsinchu (TW);
Cheng-Kuang Chen, Hsinchu (TW);
Yueh-Chun Lai, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 507 days.

(21) Appl. No.: 13/712,575

(22) Filed: Dec. 12, 2012

(65) Prior Publication Data

US 2014/0131559 A1    May 15, 2014

(30) Foreign Application Priority Data

Nov. 14, 2012   (TW) .............................. 101142402 A

(51) Int. Cl.
*G02B 1/00*     (2006.01)
*G01N 21/47*    (2006.01)
*G01N 21/552*   (2014.01)

(52) U.S. Cl.
CPC ............... *G02B 1/002* (2013.01); *G01N 21/47* (2013.01); *G01N 21/553* (2013.01)

(58) Field of Classification Search
CPC .. G02B 26/00; G02B 26/001; G02B 26/007; G02B 26/02; G02B 5/20; H01L 27/14621
USPC .............. 250/208.1, 216, 226; 359/237, 245, 359/315–320
See application file for complete search history.

(56) References Cited

U.S. PATENT DOCUMENTS

2013/0153767 A1*   6/2013   Savoy et al. ............... 250/338.1

OTHER PUBLICATIONS

Yen, Ta-Jen, and Yueh-Chun Lai, A plasmonic biosensor demonstrates high sensitivity and long-distance detection, SPIE Newsroom, DOI 10.1117/2.1201107.003782, pp. 1-3: Aug. 10, 2011.*

* cited by examiner

*Primary Examiner* — Pascal M Bui Pho
(74) *Attorney, Agent, or Firm* — Muncy, Geissler, Olds & Lowe, P.C.

(57) ABSTRACT

The present invention is related to an imaging metamaterial, comprising at least one resonant unit with a controllable split structure that comprises at least one gap and at least one segment, wherein the segment is connected by a node or separated by the gap. The present invention also provides a method for preparing an imaging metamaterial. The present invention further provides an imaging apparatus.

8 Claims, 12 Drawing Sheets
(6 of 12 Drawing Sheet(s) Filed in Color)

(a)

(b)

(c)

(d)

(e)

(a)

(b)

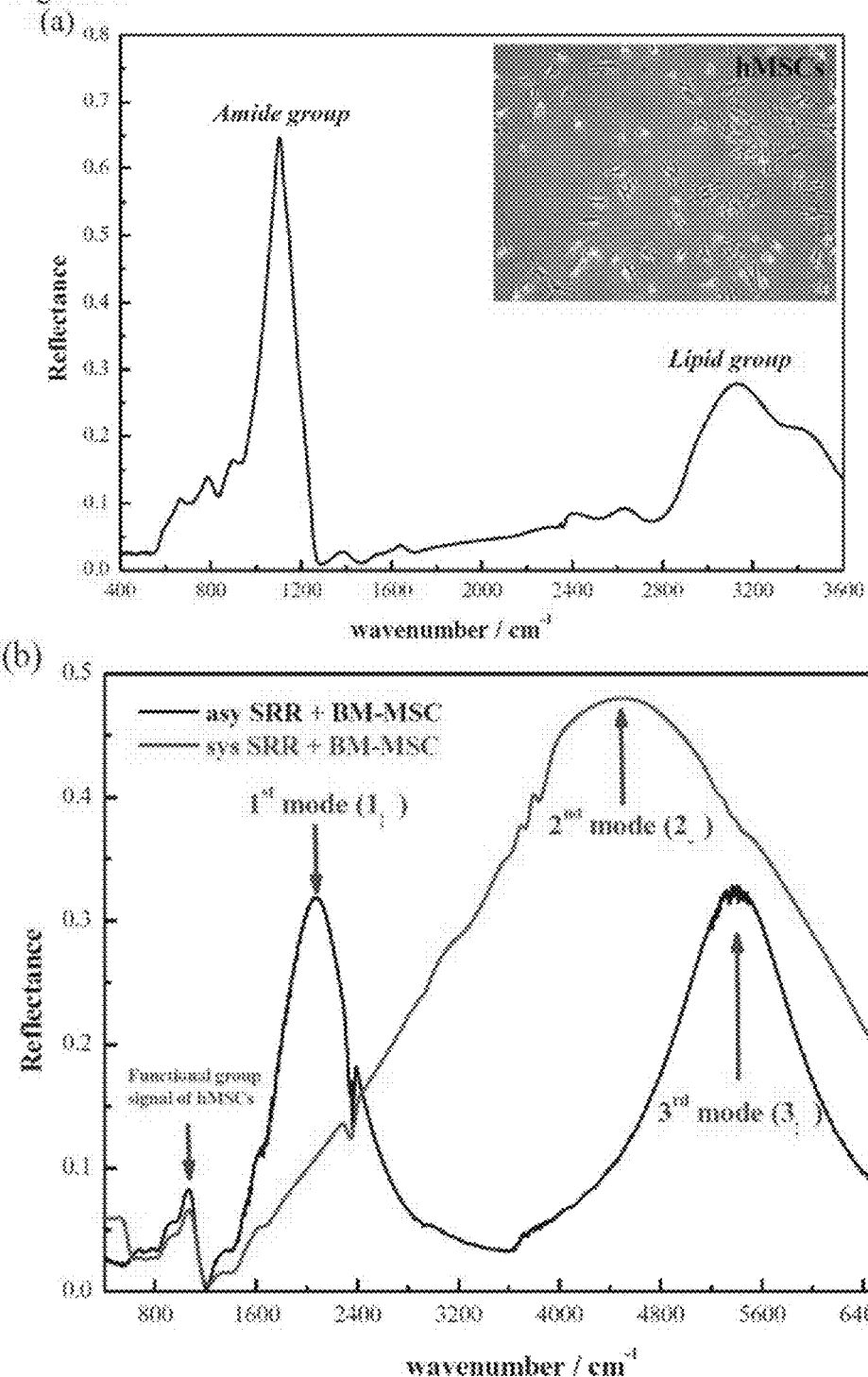

IMAGING METAMATERIAL FOR PROJECTING AN OBJECT IMAGE WITH MOLECULAR AND REFRACTIVE INDEX SIGNAL

FIELD OF THE INVENTION

The present invention relates to a label-free bio-image or an intercellular specific molecular imaging metamaterial.

DESCRIPTION OF PRIOR ART

Recent progresses in optical microscopic techniques remarkably benefit bio-imaging applications. For example, by means of confocal microscopy, stimulated emission depletion microscopy, stochastic optical reconstruction microscopy and others, these techniques enable to retrieve three-dimensional images and even to reconstruct sub-wavelength resolutions beyond the diffraction limit. Among these cutting-edge optical microscopic techniques aforementioned, a critical step requires fluorescent labeling, which is often detrimental to live cells and more critically, could affect the physiology of the cells by means of mechano-transduction. Therefore, surface plasmon resonance microscopy (SPRM), a label-free technique that images the refractive index variation of the local dielectric environment situated in the vicinity to the metal film, promises a solution to investigate the effects of biophysical stimuli exerted on cells and how cells respond to such cues in a real-time fashion. Although label-free and extremely sensitive, the SPRM still encounters several intrinsic issues—for example, the demand of optical couplers including prisms and gratings, limited operation frequency ranges typically within visible and the foremost shallow detection distances within a couple of hundreds of nanometers to impede intracellular investigation.

As a consequence, to meet the requirement of label-free, coupler-free, scalable and intracellular bio-imaging, here we present a plasmonic microscopic platform by employing multimode resonances in spilt-ring structure (SRSs). The SRSs are artificially constructed sub-wavelength structures, which allow negative magnetic permeability, high-frequency magnetism and other unprecedented electromagnetic properties based on their collective plasmonic resonances. In fact, the resonance condition of the SRS significantly depends on their local dielectric environment, so that the SRSs can be readily employed as refractive-index (RI) sensors.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 (b) illustrates the designed SRS. The dimensions of the designed SRS are a=780 nm, b=650 nm, w=100 nm and thickness of SRS equals 50 nm, respectively. Parameter L is equal to 2a+b. FIG. 9 (c) shows the normalized reflectance spectra of a designed SRS sample and the inset shows its SEM picture. The black curve (1st and 3rd mode) shows the normalized reflectance spectra with polarization direction parallel to the bar of SRS pattern; and the red curve (2nd mode) shows the normalized reflectance spectra with polarization direction perpendicular to the bar of SRS pattern. FIG. 9 (d) shows the fabricated SRS sample (top part) and the one covered by a thin layer of PMMA film spun on the surface (down part). The dimensions for both up and down figures are 165×165 $\mu m^2$, mapped by the FT-IR imaging system equipped with a focal plane array detector (64×64 detector elements) and a 15× objective (NA=0.4) with a pixel resolution of 2.7 µm. We integrated the reflectance intensity of the 1st resonant signal of our designed SRSs structure from 2200 to 2800 $cm^{-1}$, and the collected plasmonic image is displayed in false color.

FIG. 10 (b) shows the normalized reflectance spectra of designed SRS sample with hMSCs grown on surface, and FIG. 10 (c) shows the normalized reflectance spectra of fundamental mode of designed SRS structure (with hMSCs). The blue curve is the reflectance spectra of SRS structure and the green curve is the reflectance spectra of SRS structure with hMSCs grown on surface. It responds with a significant red shift in multi-mode reflectance peaks compare with only SRSs sample due to variation of dielectric environment.

FIG. 11 (b) shows the confocal fluorescent microscopic image of hMSCs. The purple part is the nuclei of hMSCs labeled by 4'-6-diamidino-2-phenylindole (DAPI). FIG. 11 (c) shows the designed SRS samples with hMSCs grown on surface sample area having been measured in a reflection mode at the wavenumber 1850-2400 $cm^{-1}$, using the FT-IR imaging system equipped with a focal plane array detector (64×64 detector elements) and a 15× objective (NA=0.4). The nucleus part of hMSCs from SRSM can be identified by comparing with FIG. 11 (b).

SUMMARY OF THE INVENTION

Figure 1:
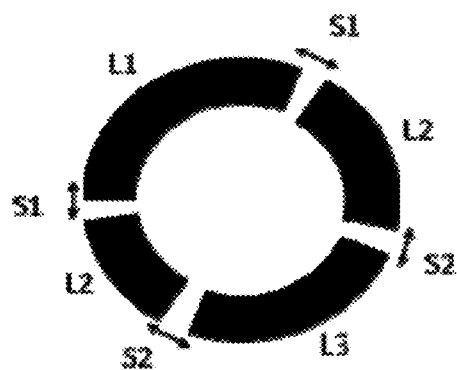
FIG. 1 (a)~(e) show controllable split structures of a resonator unit.
Figure 1:
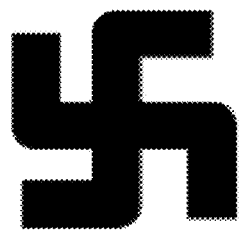
Figure 1:
Figure 1:
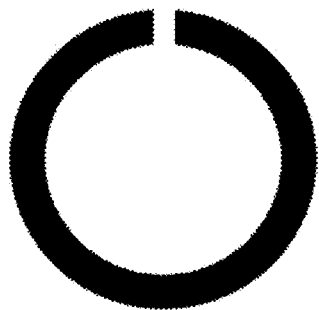
Figure 1:
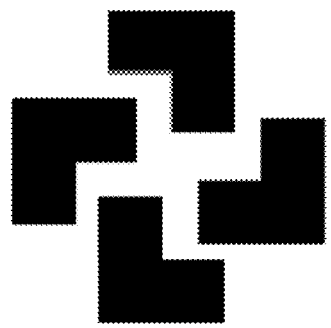

The present invention provides an imaging metamaterial comprises at least one resonant unit with a controllable split structure comprising at least one gap and at least one segment, wherein the segments is connected by a node or separated by a gap, and the resonator unit has a resonance wavelength obtained from the following formula:

$$\lambda_m = 2n_{eff}L - \lambda_0 \qquad (I)$$

where L is a length for one segment or a sum of length for all segments and gap width, $\lambda_m$ is a resonance wavelength of the resonator unit or the segment in the resonator unit, $n_{eff}$ is an effective refractive index of a dielectric environment and $\lambda_0$ is a background wavelength.

The present invention also provides an imaging apparatus, comprises:

(a) a light source for providing a light to a subject under detection to generate an electromagnetic signal of the subject;

(b) an imaging metamaterial of claim 1 for detecting the electromagnetic signal of the subject under detection, which is disposed on the imaging metamaterial;

(c) means for receiving the detected electromagnetic signal of the subject from the imaging metamaterial, and transmitting the detected electromagnetic signal of the subject to a processor; and (d) the processor for processing and generating a refractive index (RI) image or a molecular signal (MS) image based on the detected electromagnetic signal of the subject.

The present invention further provides a method for preparing an imaging metamaterial of claim 1 comprises:

(a) calculating the controllable split structure of the resonant unit using the following formula:

$$\lambda_m = 2n_{eff}L - \lambda_0 \quad (I)$$

where L is a length for one segment or a sum of length for all segments and gap width, $\lambda_m$ is a resonance wavelength of the resonator unit or the segment in the resonator unit, $n_{eff}$ is an effective refractive index of a dielectric environment and $\lambda 0$ is a background wavelength;

(b) obtaining a length of the segment or a width of the gap; and (c) forming the resonator unit of the imaging metamaterial by configuring the segment and gap obtained by step (b).

DETAILED DESCRIPTION OF THE INVENTION

The present invention provides a comprehensive imaging metamaterial comprises at least one resonant unit with a controllable split structure that comprises at least one gap and at least one segment, wherein the segment is connected by a node or separated by the gap, and wherein the resonator unit has a resonance wavelength which obtains by the following formula:

$$\lambda_m = 2n_{eff}L - \lambda_0 \quad (I)$$

where L is a length for one segment or a sum of length for all segments and gap width, $\lambda_m$ is a resonance wavelength of the resonator unit or the segment in the resonator unit, $n_{eff}$ is an effective refractive index of a dielectric environment and $\lambda_0$ is a background wavelength.

In one embodiment, the controllable split structure includes but is not limited to a ring formed by a circular segment break with at least one gap, multiple circular segment breaks with at least one gape, or linear segments connecting with a node(s) or separating by a gap. In a preferred embodiment, the controllable split structure includes but is not limited to a split-ring structure (FIG. 1a) or other split structure shown in FIG. 1b~e.

Figure 2:
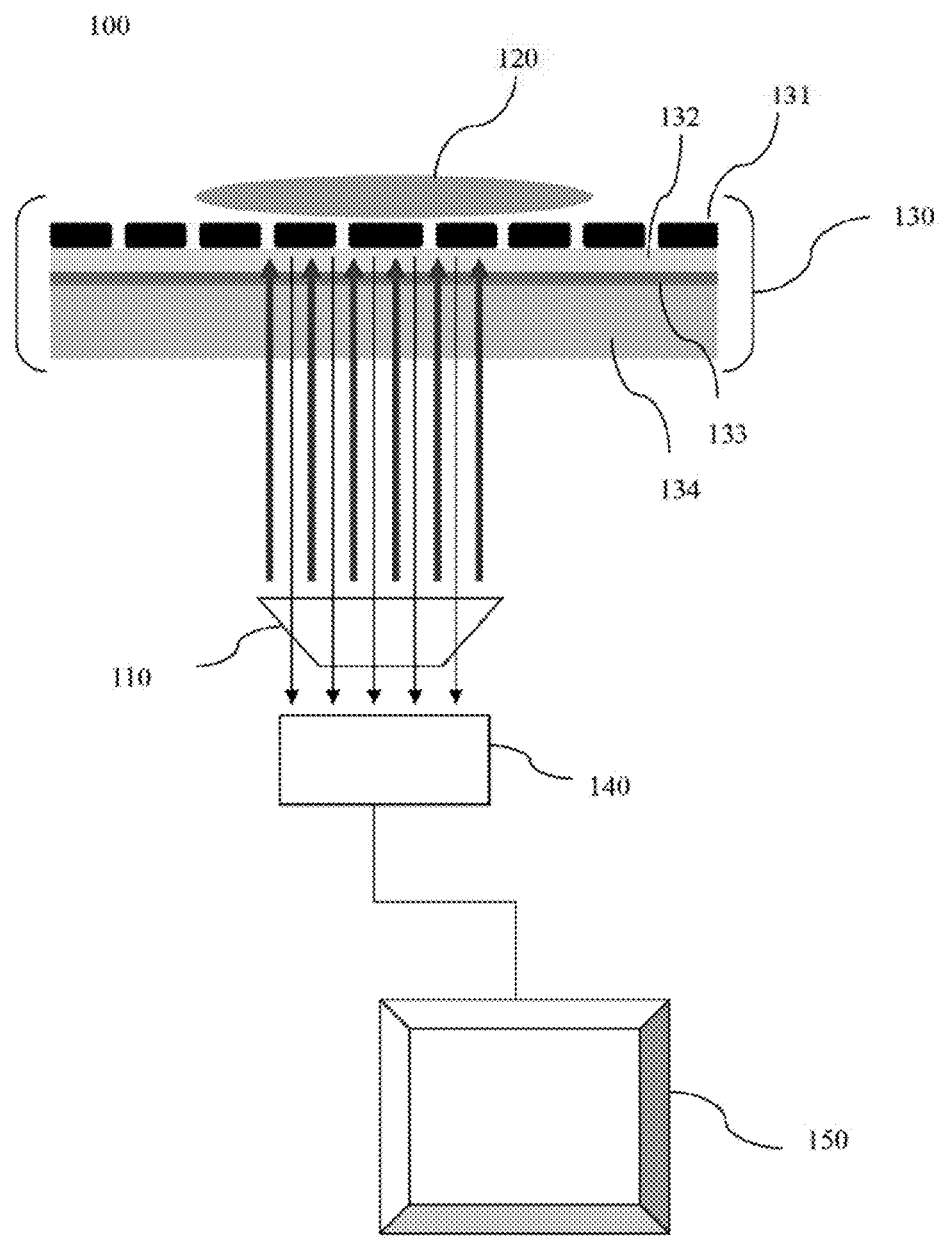
FIG. 2 shows a construction of an imaging metamaterial apparatus.
Figure 3:
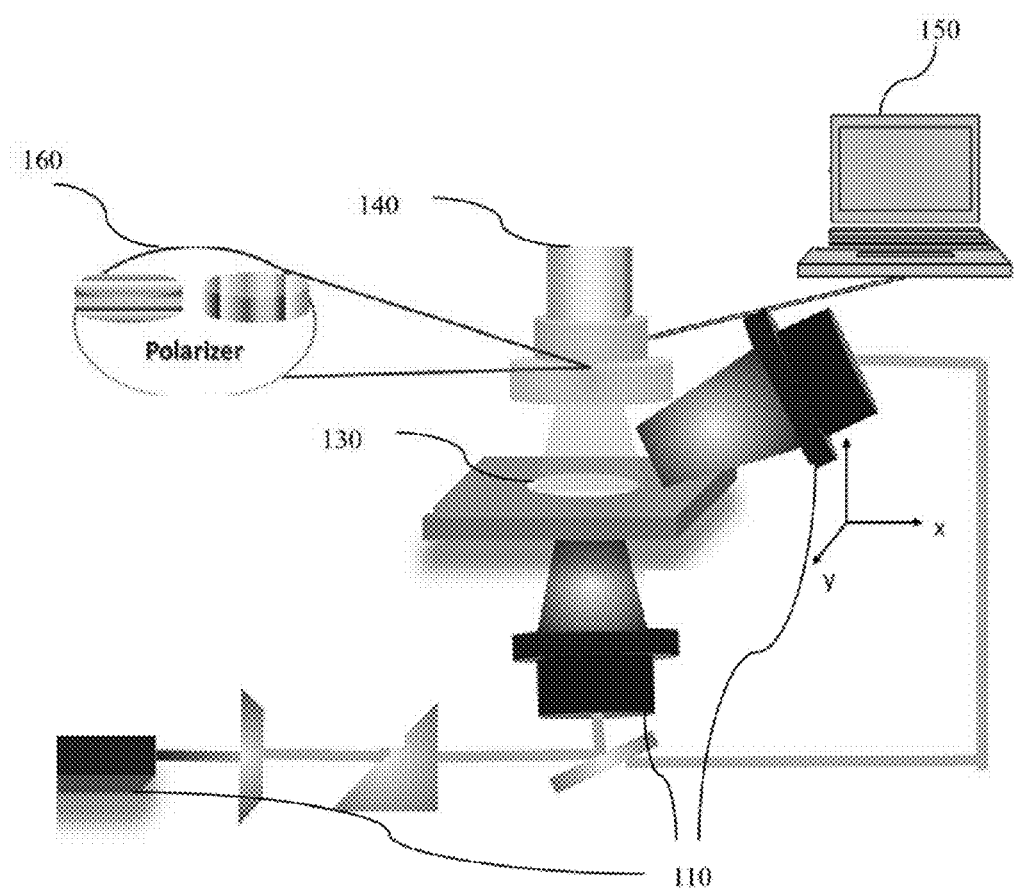
FIG. 3 shows a construction of an imaging metamaterial apparatus.

In one embodiment, the imaging metamaterial is complex with a substrate. In one preferred embodiment, the complex of the imaging metamaterial and substrate is further complex with a material of dielectric and/or metal by an adhesion layer. In a preferred embodiment, in the imaging metamaterial, the resonant unit 131 is complex with an adhesion layer 132, a dielectric 133 and substrate 134, and the dielectric 132 and metal 133 is disposed between the resonant unit 131 and substrate 134 (FIG. 2).

In other embodiment of the present invention, the segment of the imaging metamaterial is made of an electroconductive material. In one preferred embodiment, the electroconductive material includes but is not limited to metals, semiconductors, superconductor, semi-metals, porous silicon, polymers, oligomers, organic-inorganic composites, oxides, borides, carbides, nitrides, silicides, glass or combinations thereof. In one preferred embodiment, the dielectric material includes but is not limited to polytetrafluoroethylene, polyimide, polypropylene, thermoplastic materials, poly(dimethyl siloxane), ferromagnetic materials, functional transition metal oxides, pyroelectric materials, semiconductors, ferroelectric materials, or combinations thereof. Still in one preferred embodiment, the substrate includes but is not limited to a polyterafluoroethylene, polyimide, polypropylene, thermoplastic materials, poly(dimethyl siloxane), ferromagnetic materials, functional transition metal oxide, pyroelectric materials, semiconductors, ferroelectric materials, paper, silk, textile or combinations thereof.

Still in one embodiment, the resonator unit is arranged as a resonator unit array, and the imaging metamaterial comprises at least one resonator unit array.

In the present invention, the imaging metamaterial detects an electromagnetic signal of a subject under detection (abbreviated as subject), wherein the electromagnetic signal is a resonant spectrum comprising a resonant frequency and resonant intensity. In one embodiment, the electromagnetic signal further comprises a functional group resonant signal of a molecular in the subject or a refractive index signal of the subject. In one embodiment, the imaging metamaterial is used to obtain a refractive index (RI) image and/or molecular signal (MS) image of the subject.

The present invention further provides a method for preparing an imaging metamaterial comprises:

(a) calculating the controllable split structure of the resonant unit using the following formula:

$$\lambda_m = 2n_{eff}L - \lambda_0 \quad (I)$$

where L is a length for one segment or a sum of length for all segments and gap width, $\lambda_m$ is a resonance wavelength of the resonator unit or the segment in the resonator unit, $n_{eff}$ is an effective refractive index of a dielectric environment and $\lambda_0$ is a background wavelength;

(b) obtaining a length of the segment or a width of the gap; and (c) forming the resonator unit of the imaging metamaterial by configuring the segment and gap obtained by step (b).

In one embodiment, the wavelength of $\lambda_0$ is located in a range of 0.5~50 μm. In preferred embodiment, the wavelength of $\lambda_0$ is a range of 1.25~10 μm.

In a preferred embodiment, after the calculation of step (a), the present invention further calculates a periodic arrangement value of the resonator unit of the controllable structure using a collective mode resonance model via the following formula:

$$\Gamma > \lambda_{inc}/n_{eff} \quad (II)$$

where Γ is a periodic arrangement threshold value, $n_{eff}$ is an effective refractive index of the dielectric environment, and $\lambda_{inc.}$ is a resonance wavelength of incident light, in which the incident light is a light emits to the resonator unit.

The sensitivity of the imaging metamaterial can be measured by the following formula:

$$F.O.M = m(eV \cdot RIU^{-1})/fwhm.(eV) = Sensitivity \times Quality\ factor \quad (III)$$

where F.O.M is a Figure-of-Merit, m is resonance model, and fwhm. is a full width at half maximum and eV is a frequency unit.

In one embodiment, the $\lambda_m$ of formula (I) decides a resonance wavelength of a whole resonator unit or a single segment in the resonator unit. For example, when L is a sum of length for all segments and gap width(s) in the resonator unit, $\lambda_m$ is a resonance wavelength of a whole resonator unit. In the same way, when L is a length for a single segment in the resonator unit, $\lambda_m$ is a resonance wavelength of the calculated segment in the resonator unit. In further a preferred embodiment, the resonator unit comprises multiple segments, and each segment in the resonator unit has its own resonance wavelength.

In the other embodiment, the formula (II) decides the intensity of the resonance wavelength of a whole resonator unit or a single segment in the resonator unit. When the periodic arrangement value of the resonator unit is smaller than the periodic arrangement threshold value, the resonant signal of a functional group of a molecular in the subject will be further enhanced by the imaging metamaterial.

In one embodiment, the imaging metamaterial is used to obtain a refractive index (RI) image and/or molecular signal (MS) image of a subject.

The present invention also provides an imaging apparatus 100 (FIG. 2), comprising:

(a) a light source 110 for providing a light to a subject 120 to generate a electromagnetic signal of the subject under detection to generate a electromagnetic signal of the subject;

(b) an imaging metamaterial 130, for detecting the electromagnetic signal of the subject under detection which is disposed on the imaging metamaterial;

(c) means 140 for receiving the detected electromagnetic signal of the subject from the imaging metamaterial, and transmitting the detected electromagnetic signal of the subject to a processor; and (d) the processor 150 for processing and generating a refractive index (RI) image or a molecular signal (MS) image based on the detected electromagnetic signal of the subject.

In one preferred embodiment, the subject is placed on the resonant unit site of the imaging metamaterial, and the light source provides and emits the light to the substrate site of the imaging metamaterial to generate an electromagnetic signal of the subject, wherein the light includes but not limited to an infrared to a visible light. Means 140 receives the detected electromagnetic signal of the subject from the imaging metamaterial, preferably from the substrate site of the imaging metamaterial, and transmits to the processor. The processor processes and generates a refractive index (RI) image and/or a molecular signal (MS) image based on the detected electromagnetic signal.

In one embodiment, the detected electromagnetic signal is a resonant spectrum comprising a resonant frequency and resonant intensity. In other embodiment, the electromagnetic signal comprises a functional group resonant signal of a molecular in the subject or a refractive index signal of the subject. The functional group resonant signal of a molecular in the subject comprises a various specific resonant intensity peak according to the specific functional group of the molecular. The refractive index signal of the subject comprises a range of a refractive frequency of the subject.

In one embodiment, means 140 is an optical photographic system, such as an optical photographic lens. In a preferred embodiment, the optical photographic system is including but not limited to a CCD system or a focal-planar-array (FPA).

In one embodiment, the present apparatus further comprises a polarizer 160 for polarizing the detected electromagnetic signal into various polarized detected electromagnetic signals. The means 140 receives and transmits the polarized detected electromagnetic signal to the processor. In other embodiment, the polarized detected electromagnetic signal is a multi-mode resonant spectrum.

In preferred embodiment, the refractive index signal of a subject detected by the imaging metamaterial shifts compared to a background level (without a subject). When a subject has various refractive indexes of internal locations, the present imaging metamaterial will generate various shift levels of refractive index signals according to each internal location of the subject.

In one further embodiment, the processor compares the detected electromagnetic signal of the subject and background level and generates a molecular signal image or internal image of the subject. In a preferred embodiment, the processor uses the following formula to generate a computation of the detected electromagnetic signal:

$$\Delta R/R_{ref.} = |R_{analyate-TMM} - R_{bare-TMM}|/R_{ref}$$

$$\Delta T/T_{ref.} = |T_{analyate-TMM} - T_{bare-TMM}|/T_{ref} \quad (III)$$

where $R_{analyate-TMM}$ is a reflectance signal of a object detected by the imaging metamaterial, $R_{bare-TMM}$ is a reflectance signal of background detected by the imaging metamaterial, and $R_{ref}$ is a reflectance signal of reference detected by a reference mirror; where $T_{analyate-TMM}$ is a transmission signal of a subject detected by the imaging metamaterial, $T_{bare-TMM}$ is a transmission signal of background detected by the imaging metamaterial, and $T_{ref}$ is a is a transmission signal of reference detected by the substrate.

After obtaining the computation of the detected electromagnetic signal, according to the difference of computation on every internal location or a specific molecular in the subject, the processor generates an internal image or an internal specific molecular image of the subject.

In one embodiment, the subject is a light-transmissive subject. In a preferred embodiment, the subject is a crystal of a chemical, polymer, bio-organism or a part of a bio-organism. In another preferred embodiment, the subject is a cell or a tissue. In another preferred embodiment, the apparatus of the present invention is used to provide an intercellular bio-image or an intercellular specific molecular image.

EXAMPLES

The examples below are non-limiting and are merely representative of various aspects and features of the present invention.

Example 1

For a metamaterial layer, split ring structure (SRS, FIG. 1a) was chosen as an example application.

Figure 4:
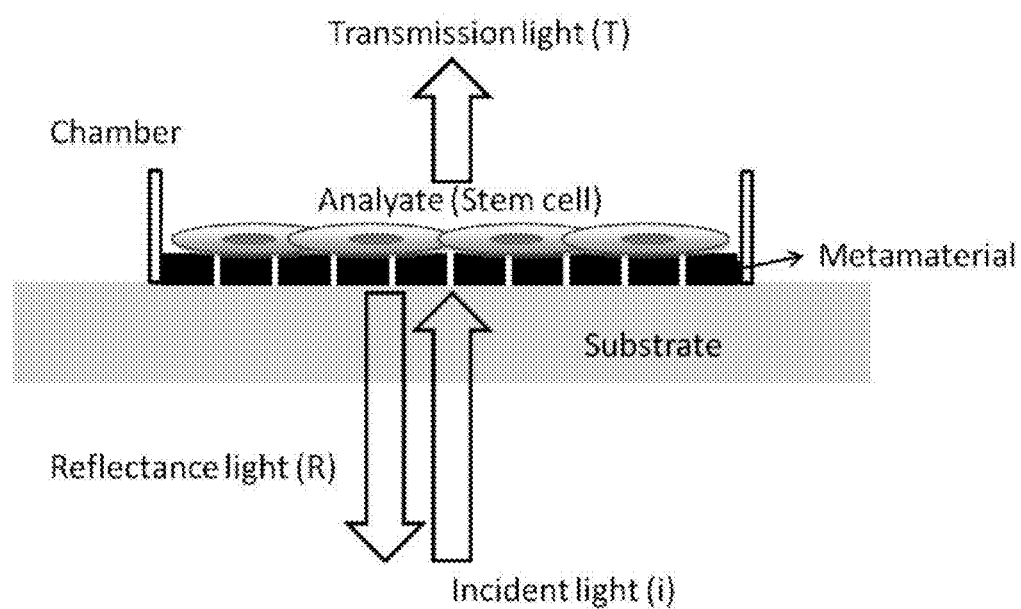
FIG. 4 shows an illustration of an imaging metamaterial apparatus.

The unit SRS was specified by segment arc length l1, l2, l3, gap width s1, s2 and total length L=l1+l2+l3+s1+s2, respectively, as shown in FIG. 1a. These parameters could tailor the plasmonic modes to match for various vibration modes of the desired molecule. The SRS, which should be dielectric or metal, and here was gold, were fabricated with a fixed unit cell ($1.2 \times 1.2 \mu^2$) for an area of $150 \times 150$ µm$^2$ through E-beam lithographic and lift-off processes, and the SRS were patterned on the electromagnetic wave penetrable substrate (Si or glass). The device was illustrated in FIG. 4.

For an analyst layer (any material), here, Human bone marrow-derived mesenchymal stem cells (hMSCs) was used. The HMSCs were grown up on the designed SRS and device, there were several function groups including C—H, C=O and C—O, whose vibration frequencies respectively located at 2920 cm$^{-1}$, 1730 cm$^{-1}$, and 1150 cm$^{-1}$.

Figure 5:
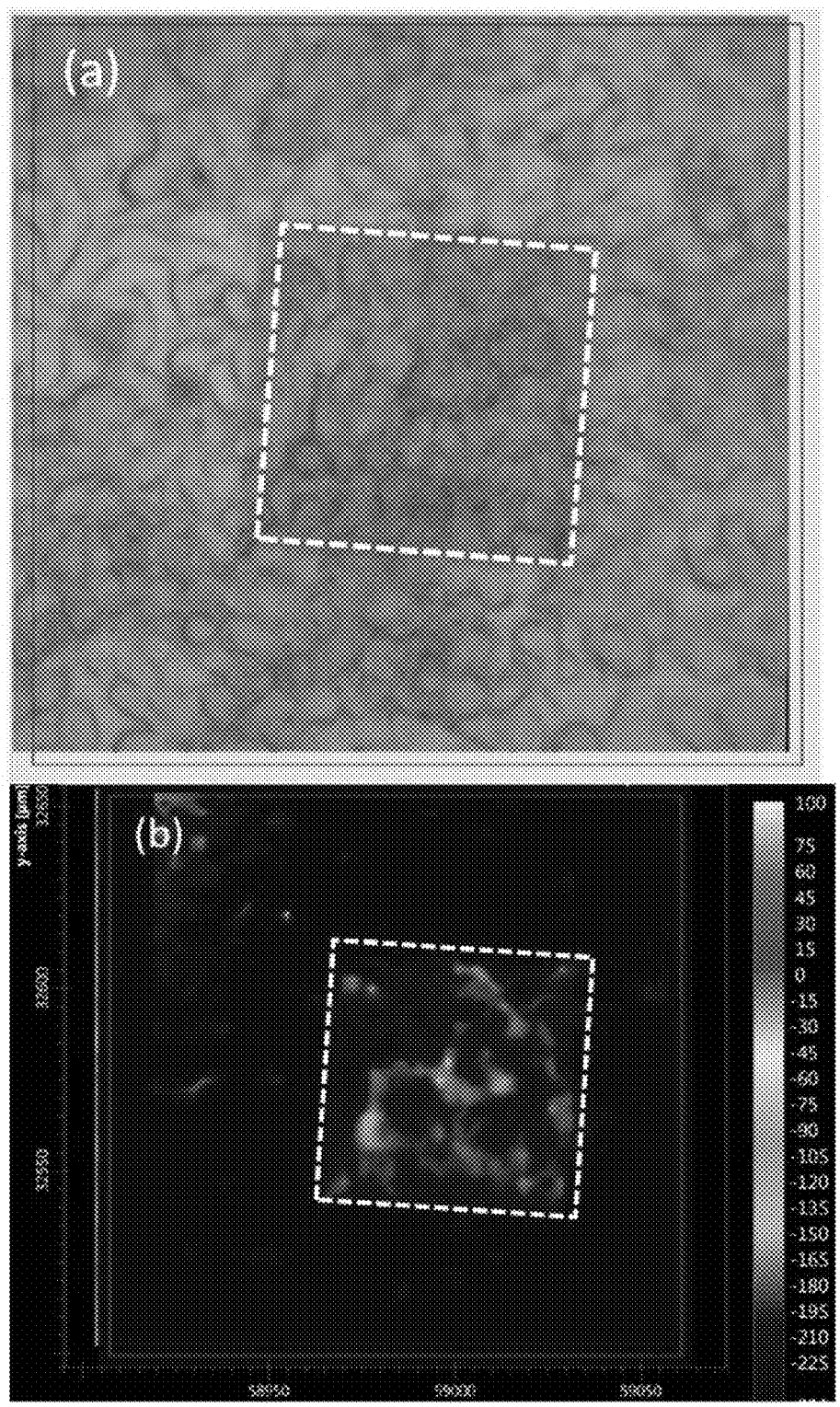
FIG. 5 (a)~(b) shows an optical image of cell membrane and FPA image of cell membrane obtained by the imaging metamaterial, wherein the dotted line shows a detecting area with the imaging metamaterial.

Then, the fabricated SRS device and analyst (stem-cell) were characterized by a micro-Fourier transform infrared spectroscopic system (µ-FTIR) with a focal planar array (FPA) in reflectance and transmittance. The optical image and FPA image of cell membrane are respectively shown in FIGS. 5a and 5b. Clearly, the FPA image showed that the stronger signals are inherent in the SRS-device-enhanced area than the other surrounding area.

Figure 6:
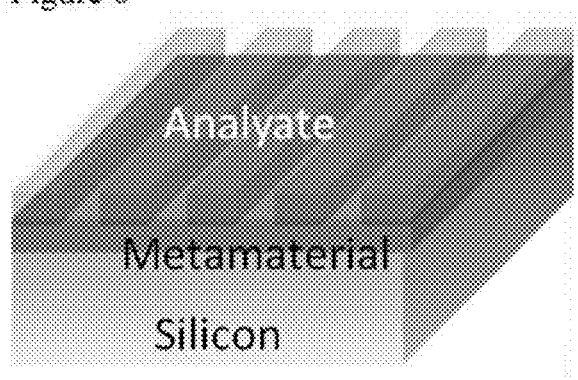
FIG. 6 shows an illustration of an imaging metamaterial apparatus.
Figure 7:
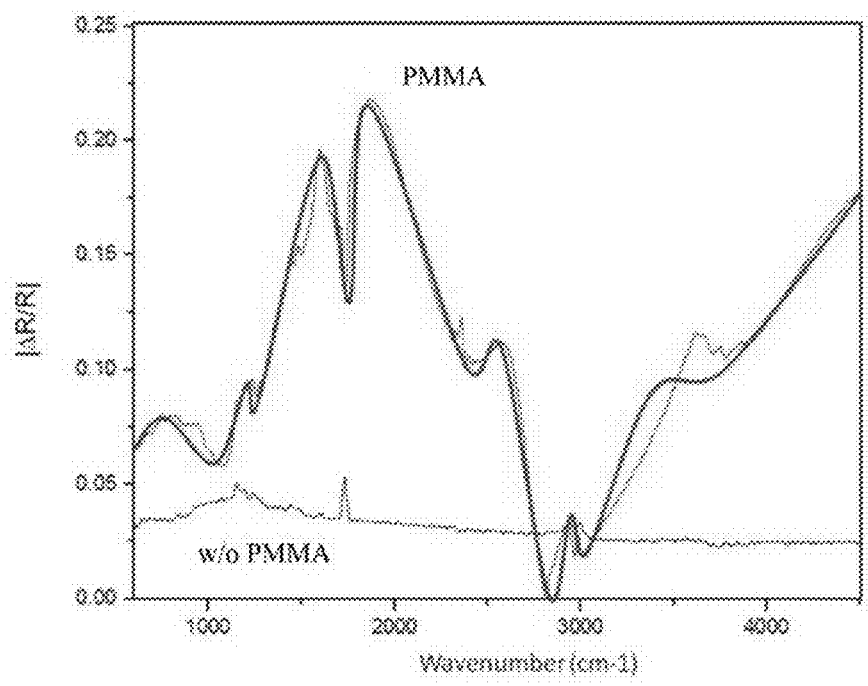
FIG. 7 shows a spectrum for calculated electromagnetic signals of PMMA and background level (without PMMA).
Figure 8:
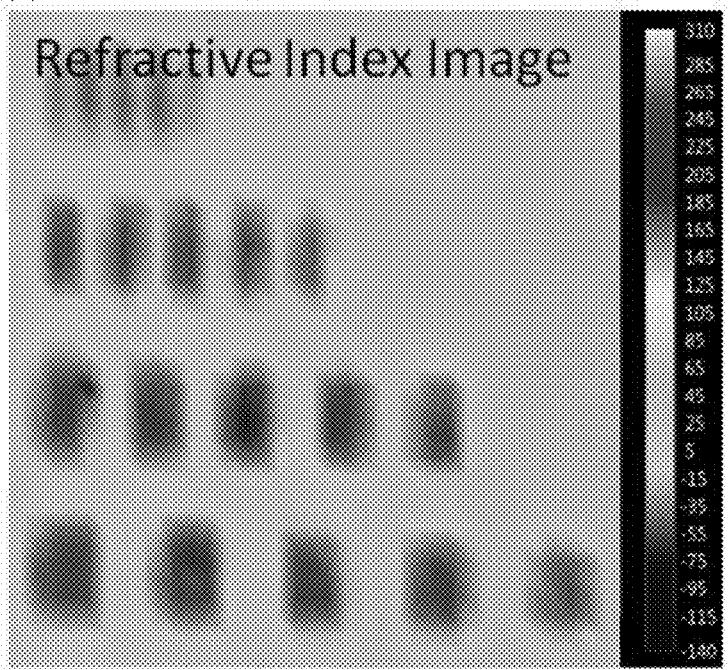
FIG. 8 (a)~(b) shows FPA images of refractive image and chemical distribution image of PMMA.
Figure 8:
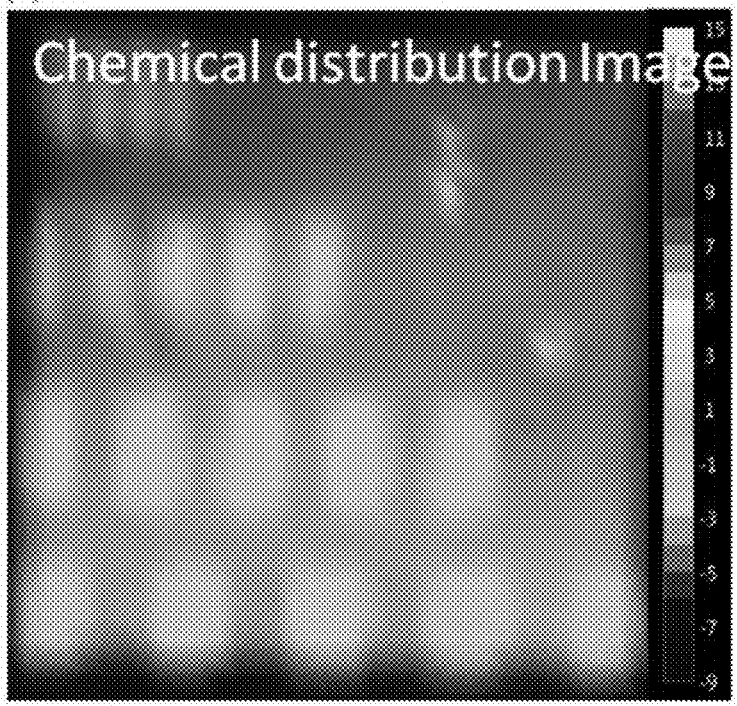

Furthermore, according to the device of the above experiment, the present invention replaced the analyst layer by Polymethylmethacrylate (PMMA). The device was illustrated in FIG. 6. The detected electromagnetic signals of PMMA and background level (without PMMA) were calculated using formula III and showed in FIG. 7. The FPA images of refractive image and chemical distribution image of PMMA were showed in FIG. 8a~8b. The PMMA signals in the SRS-device-enhanced area were stronger than the other surrounding area.

Example 2

The present invention manifested the multi-mode plasmonic resonances in the SRS, in which the lower-order modes possess greater sensitivity associated with a stronger localized electromagnetic field leading to shorter detection lengths within five hundreds nanometers, whereas the higher-order modes present mediate sensitivity with micron-scale detection lengths to allow intracellular bio-events detection. These unique characteristics of the SRS structure not only enable a multi-functional plasmonic biosensor to preserve the merits of the conventional SPR technique (e.g., label-free, excellent sensitivity, quick and real-time diagnose, detection of refractive index variations), but further promise to achieve a coupler-free, scalable and intracellular bioimaging platform.

Figure 9:
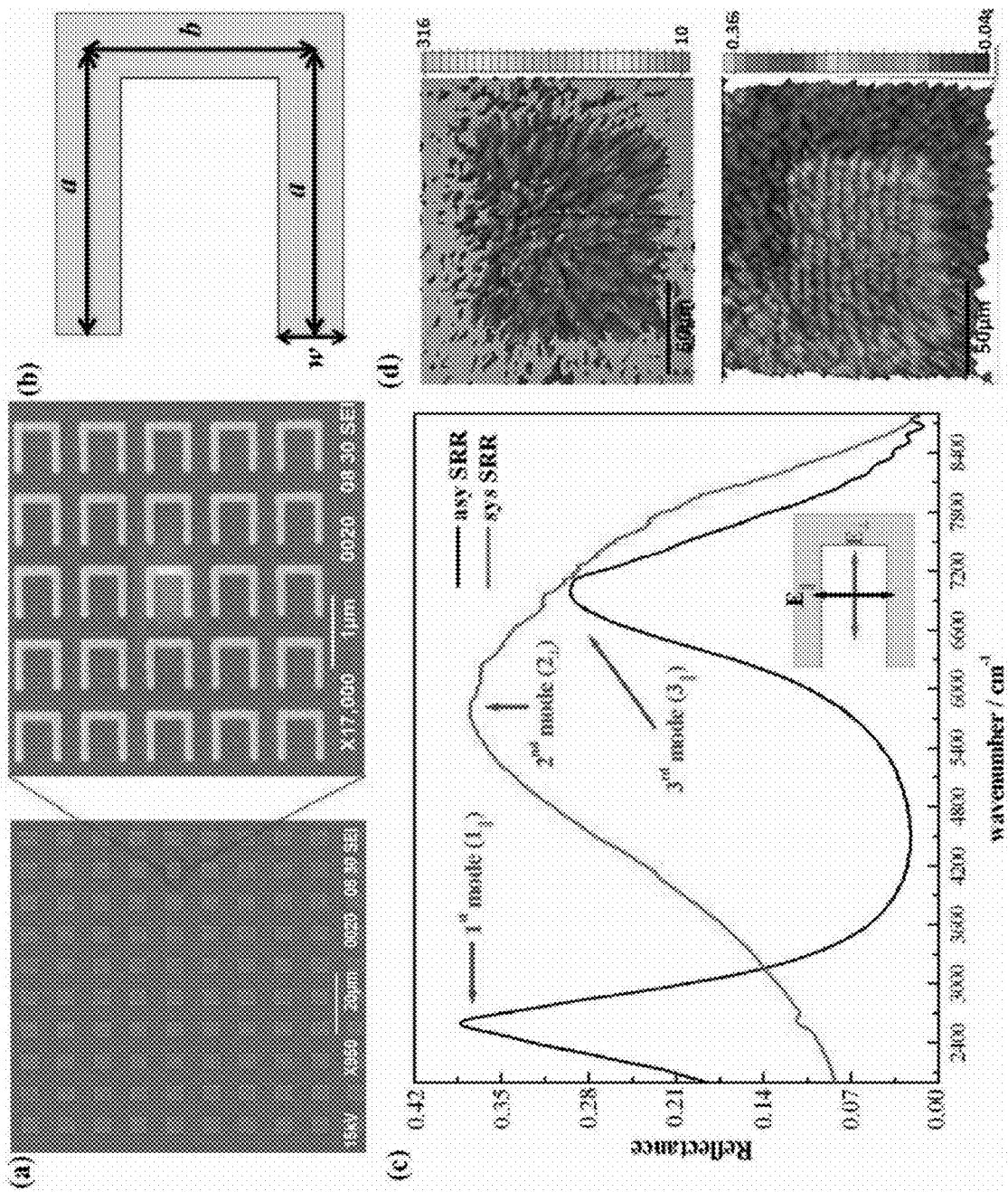
FIG. 9 (a) shows SEM images of fabricated planar SRSs. The sample consists of 5×5 SRSs as a unit cell through standard E-beam lithographic and lift-off processes.
Figure 10:
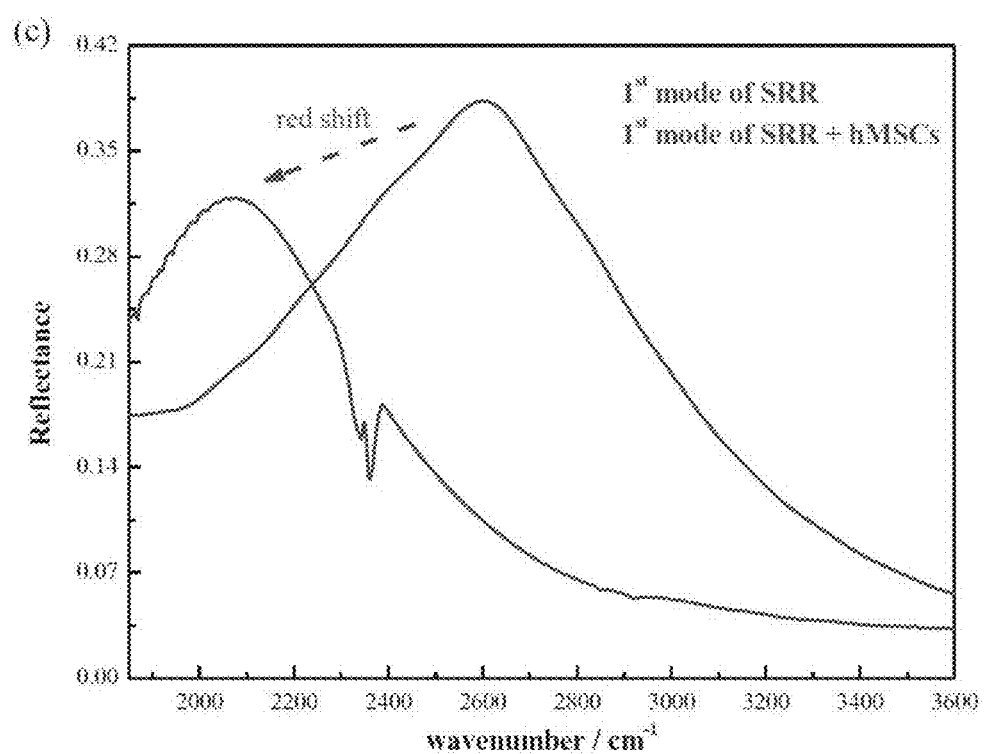
FIG. 10 (a) shows the normalized reflectance spectra of hMSCs and their optical image. Its functional group signals of biochemical components are mainly at the wavelengths of 800-1800 $cm^{-1}$ (amide group) and 2800-3200 $cm^{-1}$ (lipid), respectively.

The designed SRS samples were fabricated by standard e-beam lithographic and lift-off processes as shown in FIG. 9 a, in which one sample contains 10×10 unit cells, and each unit cell consists of 5×5 SRSs. All SRS unit cells contain exactly an identical SRS pattern from cell to cell. The parameters of designed SRS s are shown in FIG. 9 b. Besides, transmission and reflection were characterized by a Fourier-transform infrared spectrometer (Vertex 80V) equipped with an infrared microscope (Bruker Hyperion 2000) in a wavenumber range of 400-8600 cm$^{-1}$, and the corresponding mid-IR images were captured by a focal-planar-array (FPA) detector. All measured spectra have been normalized with respect to the reflection spectra of an aluminum mirror. The reflection spectrum of the SRSs at normal incidence presents three reflectance peaks, as shown in FIG. 9 c, in which the resonance wavelengths are consistent with the standing-wave plasmonic resonance (SWPR) model, and calculated via the following formula:

$$\lambda_m = \frac{2n_{eff}L}{m} - \lambda_o \qquad (IV)$$

where L is the total length of an SRS defined in FIG. 9 b, $\lambda_m$ is the resonance wavelength, m is the resonance mode, $n_{eff}$ is the effective refractive index of the dielectric environment and $\lambda_o$ depends on the geometric structure. Notice that the multiple reflectance peaks were labeled as two sets of plasmonic resonance modes: $1_{\parallel}$, $3_{\parallel}$ (asymmetry case) and $2_{\parallel}$ (symmetry case) with respect to two orthogonal E-field polarizations ($E_{\parallel}$ and $E_{\parallel}$) as shown in the inset of FIG. 9 c. We observe that the perpendicularly polarized wave ($E_{\parallel}$) excites odd modes (i.e., mode $1_{\parallel}$ at 2550 cm$^{-1}$ and mode $3_{\parallel}$ at 6900 cm$^{-1}$), and the horizontally polarized wave ($E_{\parallel}$) excites even modes (i.e., mode 2 at 5700 cm$^{-1}$), respectively. Next, the fundamental plasmonic image of the SRS was mapped by using a focal planar array (FPA) detector, and the collected plasmonic image about the SRS sample by evaluating the reflectance intensity from 2200 to 2800 cm$^{-1}$ is displayed in false color, as shown in the upper panel of FIG. 9 d. It found that the spectral signal emerges stronger within the SRS region due to the fundamental plasmonic resonance from the SRS, which served as a pixel array in the infrared region. To observe the contrast of plasmonic images, a thin layer of PMMA was spin-coated on the SRS samples and the result is shown in the lower panel of FIG. 9 d. By comparing with these two panels in FIG. 9 d, we successfully detected an obvious contrast of the plasmonic images, which stems from the refractive index variation of the local dielectric environment on this SRS platform. To further demonstrate label-free and intracellular plasmonic imaging, we cultured and collected human bone marrow-derived mesenchymal stem cells (hMSCs), and then grew the collected hMSCs on the top of the SRS substrate. The hMSCs grown on the SRS substrate exhibited both the typical flat and spindle-shaped morphology, similar to what were observed on culture flasks. Such fibroblast-like morphology remained unchanged after cells fixation, indicating the bio-compatibility of the SRS substrate. The signals of biochemical components in hMSCs mainly located at the wavenumber of 600-1800 cm$^{-1}$ (amide group) and 2800-3200 cm$^{-1}$ (lipid group), as shown in FIG. 10 a. Notice that here we carefully designed the SRS samples to avoid overlapping their operation frequencies with the intrinsic absorption signals of the biochemical components. For example, by manipulating the dimension of the SRS, we can control the fundamental resonance of the SRS samples with the hMSCs cultured atop within the wavenumber 1800-2400 cm$^{-1}$, which does not overlap with the functional group signals of hMSCs as shown in FIG. 10 b. In fact, the signals of hMSCs' main biochemical components such as proteins, carbohydrates and waxes/lipids of hMSCs can be identified by their characteristic absorption, in which the frequencies of these intrinsic signals are fixed and their intensities are weak. Yet, for bio-sensing and bio-imaging applications, one requires shiftable signals for quantitative analysis and certainly stronger signals for better performance. Now by employing our scalable SRS platform to probe the refractive index variation of the analyte, we can secure the shifted and stronger (~10 fold greater than a lipid's absorbance signal) plasmonic signals as these biochemical components appear in the vicinity of the SRS substrate. In short, differentiating with characterizing the absorption signal, the plasmonic resonance signal resting on the SRS demonstrated the advantages of stronger signal intensity, scalable resonance position, and early stage detection.

Both the reflection spectra of the fundamental mode about the bare SRS sample and the SRS sample with the cultured hMSCs atop are shown in FIG. 10 c, labeled by blue and green curves, respectively. The result responds with a significant red shift in reflectance peaks due to variation of dielectric environment, indicating that this SRS plasmonic sensor is very sensitive beyond LSPR sensors. The sensitivity (i.e., $\Delta\lambda/\Delta n$) for the 1st resonance mode of our designed SRSs plasmonic biosensor is about 2700 nm $RIU^{-1}$. In comparison with other refractive index (RI) biosensors such as surface plasmon polariton (SPP) biosensors and localized surface plasmon resonance (LSPR) biosensors, our designed SRS plasmonic biosensor possesses comparable or even better performance. For example, the sensitivity of prism coupler-based surface plasmon polariton (SPP) biosensors in wavelength interrogation ranges from 970 to 13800 nm $RIU^{-1}$, depending on the resonance wavelength, which is comparable with our SRS plasmonic biosensor. Nevertheless, these SPP biosensors require optical couplers and present shallow detection distance (typically shorter than a couple of hundred nanometers), so that their applications in bio-imaging turn to be limited; besides, the sensitivity of localized surface plasmon resonance (LSPR) biosensors is from 120 nm $RIU^{-1}$ to 500 nm $RIU^{-1}$, which performs much worse than the demonstrated SRS plasmonic biosensor. This SRS plasmonic biosensor performs similar to the hybridization of surface plasmon polariton (SPP) and localized surface Plasmon resonance (LSPR), in which the former is non-radiative and owns better sensitivity, and the latter is radiative and possesses poor sensitivity. For instance, the lower-order modes resemble SPP are more sensitive but with shorter sensing depths of sub-micron scales due to the non-radiative nature of SPP; in contrast, the higher-order modes favor LSPR to demonstrate less sensitivity yet greater sensing distances up to micron scales due to the radiative nature instead. Such a significant change of resonance peaks due to the local attachment of cells has not been well studied in the metamaterial community. In the invention, biomolecular sensing measurements demonstrate the possibility for sensitive detection and correlation between the peak shift and the length in a vertical direction from the SRS surface to inner structure of cells.

In summary, we present a first-ever intracellular plasmonic imaging by exciting multi-mode resonances in spilt-ring resonators. Human bone marrow-derived mesenchymal stem cells (hMSCs) are the target to be observed in our platform. The invention successfully demonstrates the feasibility of using SRSM for constructing the refractive index distribution of hMSCs to achieve an intracellular bio-imaging platform, while obtaining the information of functional groups from the target cells. The demonstrated SRSM possesses the key advantages beyond other optical microscopy, such as label-free and real-time diagnosis (vs. fluorescent and Raman scattering techniques), coupler-free to avoid the issues of coupling oil leakage and dispersion, great detection lengths (vs. SPP techniques), and scalable operation frequencies (vs. LSPR techniques) in particular in IR regimes to prevent strong absorption from bio-agents, while providing the possibility for the live cells imaging technique, including the observation of cellular proliferation and differentiation process.

Example 3

The present invention designed the SRS sample and measured it by using a Fourier transform infrared spectrometer (Vertex 80V) equipped with an infrared microscope (Bruker Hyperion 2000) in the wavenumber range of 400-8600 $cm^{-1}$, and the corresponding mid-IR images were captured by a focal-planar-array (FPA) detector. Due to the usage of modern focal plane array detectors, it has advanced to a new imaging technique. First, the SRS sample was measured and then a poly methyl methacrylate (PMMA) was spin-coated on the SRS sample to observe the contrast of image with/without the PMMA for test. Successfully, obvious image contrast can be obtained in the present platform. Next, the present proposed platform was used to construct a bio-image of hMSCs. In order to observe hMSCs, the SRS sample was carefully designed based on the standing wave plasmonic resonance model whose operated resonance frequency is within mid-infrared region and avoid the overlap with functional groups signals of hMSCs. Then, hMSCs were grown up on the designed SRS sample. Finally, this highly sensitive SRS microscopy (SRSM) platform was utilized to obtain refractive index images of hMSCs.

Human bone marrow-derived MSCs (hMSCs) were acquired as described previously and bone marrow samples were collected after Institutional Review Board approval. hMSCs were cultured in a commercially available expansion medium MesenPRO (Invitrogen, Grand Island, N.Y., USA) with penicillin (100 units $mL^{-1}$), streptomycin (1,000 units $mL^{-1}$) and L-glutamine (2 mmol $L^{-1}$; Sigma-Aldrich, St. Louis, Mo., USA). hMSCs ($5\times10^4$ cells $mL^{-1}$) were seeded and cultured on the designed SRS sample for 72 h. The hMSCs on the SRS sample were gently washed with phosphate buffered saline and were fixed in 4% paraformaldehyde for 20 min.

For immunofluorescent staining of hMSC, hMSCs seeded and cultured on glass for 72 h, and the cells were fixed in 4% paraformaldehyde for 20 min, permeablized with 0.2% triton X-100 in PBS and blocked with 1% goat serum in PBS. And then, fixed cells were immunostained with 4'-6-diamidino-2-phenylindole (DAPI) for nuclear double stranded DNA. The mounting and images were taken by an inverted confocal fluorescence microscope.

Example 4

Bioimage of hMSCs was based on the fundamental resonance signal ($1_{\parallel}$ mode) of SRS at the wavenumber of 1850-2400 $cm^{-1}$ that fits in the detection range of the FPA detector (900-3600 $cm^{-1}$). Both conventional optical microscopic and confocal optical microscopic images were also presented for controlled comparison.

Figure 11:
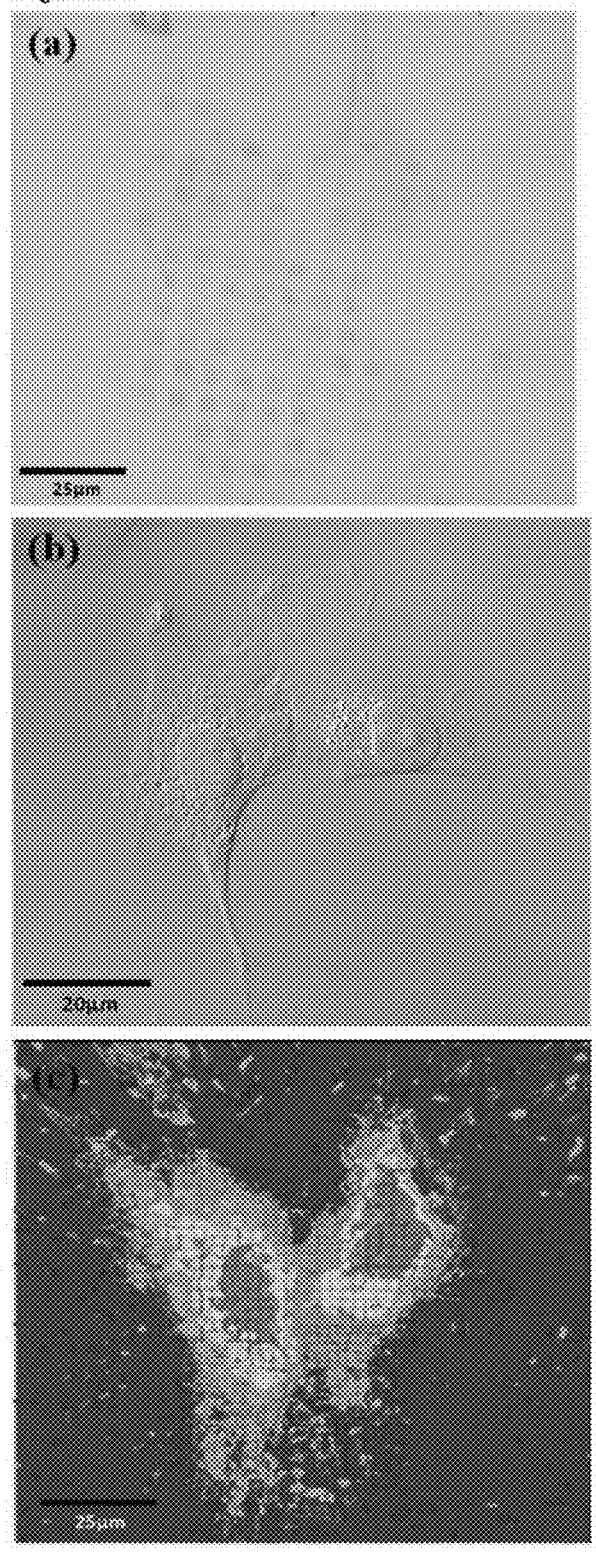
FIG. 11 (a) shows the unlabeled optical microscopic image of hMSCs on the SRS substrate.

FIG. 11 a shows a conventional optical microscopic image of hMSCs grown on the SRSs samples and the black part in the background refers to the SRSs structure. In this case, we cannot reveal any detail of an inner nucleus and organelles without the labeling process. FIG. 11 b shows the confocal fluorescent optical microscopic image of hMSCs, in which we can observe the nuclei of hMSCs, wherein the purple part labeled by 4'-6-diamidino-2-phenylindole (DAPI). Nevertheless, such a labeling process is typically expensive and time consuming, while impeding the practical application of real-time diagnosis. Besides, for the biological reaction sensitive to the three-dimensional structure of biomolecules, the labeling process of introducing fluorescent markers to the target will radically affect the analytic result. As a consequence, the invention construct an intracellular image of hMSCs by the SRS platform instead, which does not require the labeling process aforementioned, but directly detects the change of plasmonic resonance of the SRS fluctuated by the local attachment of the targeting bio-agents. The result was shown in FIG. 11 c, displaying the plasmonic image of hMSCs cultured on the SRSs sample by evaluating the reflectance intensity within the wavenumber of 1850-2400 cm$^{-1}$. Clearly, we observe evident intracellular contrast resting on the refractive index distribution of hMSCs in the present system. For example, the nucleus, a membrane-bound organelle that is densely comprised of nucleic acids and proteins associated with a substantially higher refractive index than the surrounding cytoplasm, can be thus easily visible as presented in red corresponding to the greatest shift of resonance frequencies and the strongest reflection intensity. Besides, the other colored parts mainly refer to the cytoplasm, corresponding to the smaller shift of resonant frequencies stemming from the lower refractive index of the cytoplasm. In short, the morphologic observation by the label-free SRSM exhibits the similar result to the confocal fluorescent optical microscopy image (as shown in FIG. 11 b). The image of individual organelles within the cytoplasm of hMSCs could be further identified by employing asymmetrically coupled SRSs structures to enhance the Q-factor of the plasmonic resonance.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The detecting samples (such as cells or PMMA), the apparatus and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. An imaging metamaterial consisting of a resonant unit with a controllable split structure, an adhesive layer, a dielectric material, a substrate and a culture medium, wherein a sequential order, from top to bottom, are following: the culture medium, the resonant unit, the adhesive layer, the dielectric material and the substrate, wherein the controllable split structure consists of at least one gap and at least one segment, wherein the at least one segment is connected by a node or separated by a gap, and the resonant unit has a resonance wavelength obtained from the following formula:

$$\lambda_m = 2n_{eff}L - \lambda_0 \quad (I)$$

wherein L is a length for one segment or a sum of length for all segments and gap width, $\lambda_m$ is a resonance wavelength of the resonant unit or the segment in the resonant unit, $n_{eff}$ is an effective refractive index of a dielectric environment and $\lambda_0$ is a background wavelength, and wherein the at least one segment is made of an electroconductive material.

2. The imaging metamaterial of claim 1, which reflects an electromagnetic signal of a subject for detection.

3. The imaging metamaterial of claim 2, wherein the electromagnetic signal is a resonant spectrum comprising a resonant frequency and resonant intensity.

4. The imaging metamaterial of claim 2, wherein the electromagnetic signal comprises a functional group resonant signal of a molecular in the subject or a refractive index signal of the subject.

5. The imaging metamaterial of claim 2, wherein the electromagnetic signal comprises a functional group resonant signal of a refractive index signal of the subject.

6. The imaging metamaterial of claim 5, which is used to obtain a refractive index (RI) image of the subject.

7. The imaging metamaterial of claim 6, which is used to obtain a molecular signal (MS) image of the subject.

8. A method for preparing the imaging metamaterial of claim 1, wherein the method comprises:
   (a) calculating a length of a segment or a width of a gap for constructing the controllable split structure of the resonant unit of the imaging metamaterial using the formula;
   (b) obtaining the length of the segment or the width of the gap, wherein the segment is made of the electroconductive material;
   (c) forming the resonant unit of the imaging metamaterial by configuring the segment and gap obtained by step (b); and
   (d) adding the culture medium on the resonant unit and adding the adhesive layer, the dielectric material and the substrate under the resonant unit to form the imaging metamaterial.

* * * * *